United States Patent [19]
Whiteside

[11] Patent Number: 6,066,120
[45] Date of Patent: *May 23, 2000

[54] FLUSHABLE SOLUBLE MEDICO-SURGICAL BAGS

[75] Inventor: Neil Adrian Whiteside, Steyning, United Kingdom

[73] Assignee: Smiths Industries Public Limited Company, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/060,963

[22] Filed: Apr. 16, 1998

[30] Foreign Application Priority Data

Apr. 30, 1997 [GB] United Kingdom ............... 9708783

[51] Int. Cl.⁷ ........................................ A61F 5/44
[52] U.S. Cl. .................. 604/332; 604/349; 128/DIG. 24
[58] Field of Search ..................... 604/332, 349, 604/328; 128/DIG. 24

[56] References Cited

U.S. PATENT DOCUMENTS

| | | |
|---|---|---|
| 4,035,540 | 7/1977 | Gander . |
| 4,946,720 | 8/1990 | Oishi et al. ............... 604/332 |
| 5,578,023 | 11/1996 | Schneider ................. 604/332 |

FOREIGN PATENT DOCUMENTS

| | | |
|---|---|---|
| 0010171 | 4/1980 | European Pat. Off. . |
| 0010171a | 4/1980 | European Pat. Off. . |
| 0226439 | 6/1987 | European Pat. Off. . |
| 0684028A1 | 11/1995 | European Pat. Off. . |
| 2195919A | 4/1988 | United Kingdom . |
| 2211196A | 6/1989 | United Kingdom . |
| 2257056A | 1/1993 | United Kingdom . |

*Primary Examiner*—Mark O. Polutta
*Attorney, Agent, or Firm*—Pollock, Vande Sande & Amernick

[57] ABSTRACT

A wc-disposable ostomy bag has walls made of three layers. The central layer is of an alkali-soluble/water-resistant material such as carboxylated acrylic polymer and is about 100μ thick. The inner layer, presented to the contents of the bag, is of a water-resistant, ordor-proof material such as polyvinylidene chloride and is between about 2 and 3μ thick. The outer layer is a non-woven material such as formed by cellulose fibres in a binder of aqueous polyacrylate, which is broken up when wetted by an alkaline liquid.

8 Claims, 1 Drawing Sheet

FLUSHABLE SOLUBLE MEDICO-SURGICAL BAGS

BACKGROUND OF THE INVENTION

This invention relates to wc-disposable bags.

There are several important criteria that must be satisfied by an ostomy bag. Firstly, it must be highly ordor proof over the entire period for which it is worn and in all circumstances of varying temperature and humidity etc. Secondly, the bag must be inconspicuous from outside the wearer's clothing. For this reason, the bag material must not rustle or make other noises when the wearer moves. The bag should also be thin and flexible so that it conforms to the wearer's anatomy without producing bulges or ridges beneath the clothing. Thirdly, the bag must be reliable and secure so that the wearer can have high confidence that the bag will not tear or come apart at the edge seal during use. Fourthly, the bag must be affordable, which means that it must be able to be made at low cost.

Attempts have been made recently to develop ostomy and urine bags which can be disposed of by flushing in a wc, to avoid the need to make special disposal arrangements, which can be inconvenient, embarrassing and unhygenic.

Where a bag is also required to be wc disposable, this adds further difficulties to the choice of materials and manufacturing techniques, since the bag must possess all the above properties while also being capable of being disposed of by flushing in a wc. The problems are further compounded if the bag must be resistant to water, so that it can be worn safely in wet conditions. The selection of appropriate combinations of different materials that enables a bag to satisfy these requirements requires considerable skill and experiment.

WC-disposable bags have been proposed in the literature, the bags having an outer water-soluble or dispersible layer and an inner water-resistant layer. The outer layer provides mechanical support for the inner layer so that, when the bag is dropped into turbulent water in a wc pan, the outer layer is quickly broken up. The inner layer prevents the contents of the bag attacking the outer layer in use but, once the outer layer is broken up on disposal, the inner layer does not have sufficient mechanical strength in itself to cause blockage on flushing the wc An example of such a bag is described in GB 2083762B. A wc-disposable bag is sold by SIMS Portex Limited, England under the name Symphony (Symphony is a Registered Trade Mark of SIMS Portex Limited).

Although such bags can be used satisfactorily, the fact that the outer layer is damaged by contact with water means that the user has to take special precautions to ensure that the outside of the bag does not become wet. This can be especially inconvenient with bags which are worn long-term, for two or more days, such as is usually the case with ileostomy bags. The use of such bags can make washing difficult and prevents the user swimming.

An alternative form of bag is described in EP 0142950A, which is made of 3-hydroxybutyrate film, either in a laminate with a water-soluble film as an outer layer, or entirely from 3-hydroxybutyrate. Such a material remains intact when in contact with water or body waste, but is broken up if the pH is raised to about 12. The bag described is disposed of by adding a base material to the contents of the bag so as to raise the pH of the contents to at least 12 so that it breaks up when agitated in a we pan. The laminated construction would not avoid the disadvantages referred to above of having to keep the outside of the bag dry. Furthermore, 3-hydroxybutyrate does not provide sufficient ordor barrier properties to be useful in a practical bag.

A further alkali-disposable bag is described in GB 2195919B. The walls of this bag have a central layer of polyvinyl alcohol, an inner layer of a blend of polyvinylidene chloride acrylonitrile copolymer with carboxylated acrylic copolymer, and an outer layer of two or more coatings of carboxylated acrylic acid. This bag can be disposed of in a wc by adding an alkali to the water in the pan. The material proposed for the inner layer combines the alkali-solubility of carboxylated acrylic copolymer with the high ordor barrier properties of polyvinylidene chloride acrylonitrile copolymer, the blend being water resistant. However, in practice it has been found difficult to produce an inner layer having sufficiently high ordor barrier properties while also being broken up quickly in alkali. Furthermore, the polyvinyl alcohol central layer is difficult to coat because the high resistance of polyvinyl alcohol to organic solvents produces a weak interply adhesion. Attempts to use an aqueous-based coating material have not been entirely satisfactory because the polyvinyl alcohol abstracts the water from the coating too quickly to enable a high quality film to be produced. Although it is possible to produce bags according to GB 2195919B that will function, their speed of disposability and ordor barrier properties are not as good as would be desired.

Another alkali-disposable bag is described in GB 2257056. This bag has an outer layer substantially entirely of alkali-soluble/water-insoluble carboxylated acrylic polymer forming a major part of the thickness of the material and a thinner, inner layer of alkali-resistant polyvinylidene chloride bonded directly to one side of the first layer. One problem with this bag is that the outer layer can in some cases become softened by the warmth and humidity of the wearer's body, causing the bag to be deformed by its weight and that of its contents. This can lead to damage to the inner layer and leakage of ordor.

BRIEF SUMMARY OF THE INVENTION

It is an object of the present invention to provide an improved medico-surgical bag.

According to the present invention there is provided a wc-disposable bag having walls made substantially from a material comprising a first layer substantially entirely of alkali-soluble/water-resistant material, a second, thinner layer of water-resistant material bonded to one side of the first layer and presented inwardly of the bag and a third layer bonded to the first layer on the side remote from the second layer, the third layer being presented outwardly of the bag and being of a non-woven material that breaks down when wet so that the bag can be disposed of in a wc by adding an alkali to water in the wc pan, thereby causing the third layer to break down and allowing the alkali to break up or disperse the first layer, and the thickness of the second layer being insufficient to impede flushing of the bag after break up or dispersion of the first and third layers but being sufficient to provide the major part of the ordor barrier of the bag and to reduce ordor transmission through the material to an acceptable level.

The first layer may be of carboxylated acrylic polymer and be approximately $100\mu$ thick. The second layer may be of polyvinylidene chloride and be approximately 2 to $3\mu$ thick. The third layer when intact preferably resists mechanical deformation of the bag by the weight of its contents. The third layer may include cellulose fibres and be of a material that is broken down only when wetted by an alkaline liquid. The third layer may include a binder of aqueous polyacrylate and have a thickness equivalent to about 30 gsm. The bag may include a coloring agent.

A wc-disposable ostomy bag and its method of manufacture, in accordance with the present invention, will now be described, by way of example, with reference to the accompanying drawings.

DETAILED DESCRIPTION OF THE PREFERRED EMBODIMENT

Figure 1:
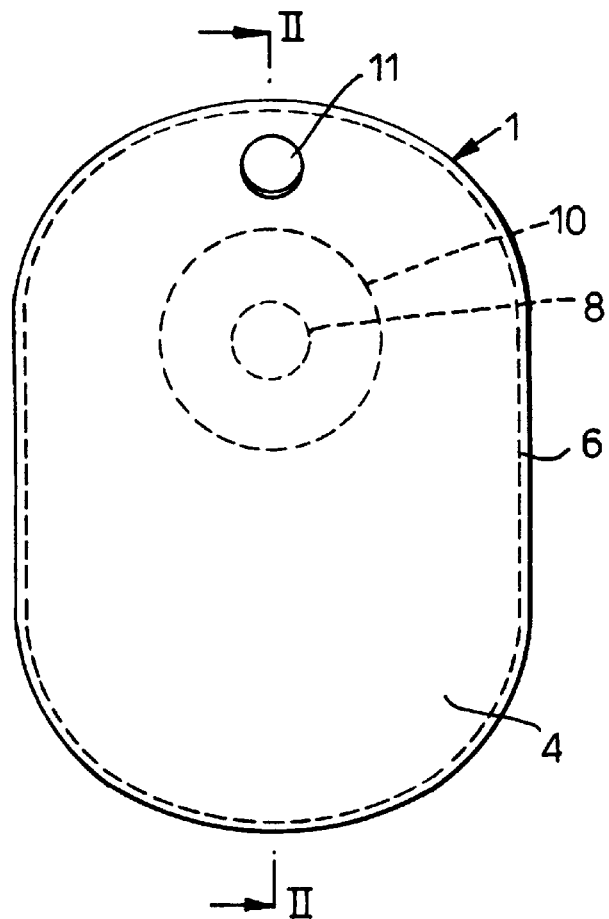
FIG. 1 is a front elevation view of the ostomy bag.
Figure 2:
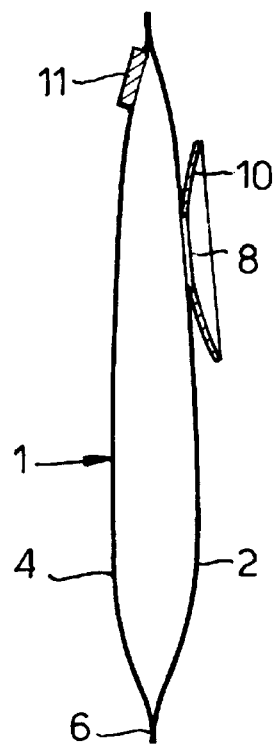
FIG. 2 is a sectional side elevation along the line II—II of FIG. 1.

The ostomy bag 1 is of conventional shape and comprises two walls or sheets 2 and 4 of the same material heat sealed together around their outer edge 6. The sheet 2, which, in use, faces the wearer, has an orifice 8 forming an opening to the bag. An adhesive flange 10 is secured to the sheet 2 around the orifice 8; this serves to secure the bag to the user's skin around the stoma so that fecal matter is discharged into the bag. A filtered vent 11 is located towards the top of the bag 1.

Figure 3:
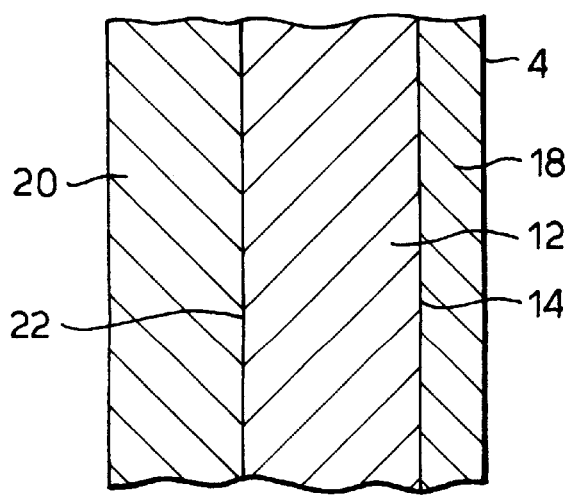
FIG. 3 shows a part of FIG. 2 to an enlarged scale.

The material from which both sheets 2 and 4 are made is shown in greater detail in FIG. 3. FIG. 3 shows the relative thickness of the layers to a correct scale. The sheets 2 and 4 comprises three layers. A first continuous, imperforate layer 12 is of carboxylated acrylic polymer of the kind sold by Belland AG under Grade No. 100H40LB. Typically, the layer 12 is about 100 micron thick. One surface 14 of the layer 12 has a coating in the form of a continuous, imperforate second layer 18 of polyvinylidene chloride, which is about 2–3 micron thick, that is, thin compared with the layer 12. The second layer 18 is presented inwardly to the contents of the bag 1 on both sheets 2 and 4. Because polyvinylidene chloride provides a very effective ordor barrier, it is only necessary to use a very thin layer, even though the layer 12 of carboxylated acrylic polymer has very poor ordor barrier properties. The third layer 20 is formed on the opposite surface 22 of the layer 12 and is of a non-woven material with a thickness equivalent to about 30 gsm. The nature of the non-woven material forming the third layer 20 is selected to provide stability to the underlying layer 12 when dry but to break down when wet. There are various forms of non-woven material that can be used. For example, it could be a tissue paper formed of cellulose fibres held together by a water-soluble binder, such as poly(vinyl alcohol). Such a material would be broken up by water, without the need for an alkaline. Alternatively, the material could be a non-woven material incorporating an alkali-soluble binder. The non-woven fibres could be formed from a wide range of polymers, or blends of different types, such as cellulose and polyester. The alkali-soluble binder could be a polymer that can be applied from solution during the production of the non-woven material. More particularly, aqueous polyacrylate dispersions such as that available from Belland AG under the reference DBC 2620 could be used.

The layers 12 and 18 are formed in a conventional manner, such as that described in GB2257056, and the non-woven layer 20 is applied to the outer surface 22 of the first layer 12 by adhesive lamination. Alternatively, the layer 12 could be coated onto the non-woven layer 20 from solution, or by extrusion coating, the inner layer 18 being applied subsequently.

The material forming the walls 2 and 4 could contain a dye or pigment incorporated in any of the layers 12, 18 or 20, or in adhesive between the layers. The dye colors the water in the wc pan during disposal, in order to confirm to the user that the bag is dissolving. The dye could be sensitive to pH so that it is initially colorless and then develops color at high pH. Alternatively, the dye could change from one colour to another on addition of the alkali.

The bag is made by cutting sheets 2 and 4 from the material and placing them with their polyvinylidene chloride layers 18 facing one another prior to heat sealing them together around their outer edge 6. The good interply adhesion between the layers 12 and 18 ensures that the weld strength of the seal around the edge 6 of the bag is high. The flange 10 may then be attached by an adhesive.

The bag 1 is used in the conventional way. The outer, non-woven layer 20 keeps the plastics layer 12 away from direct contact with the patient's skin, thereby reducing its exposure to perspiration. Water vapor, however, can pass through the outer layer 20 to the underlying layer 12 and this, combined with the warmth of the body may lead to some softening of the central layer 12. The outer layer 20, however, provides a mechanical reinforcement to the central layer 12, thereby increasing its structural integrity and preventing it being stretched or deformed by the weight of the bag and its contents. This is important because the inner layer 18 is very thin and any deformation in the bag 1 could cause ruptures in this layer, leading to the escape of ordor.

The material of the sheets 2 and 4 is flexible and noise free so that the bag will lie flat and remain inconspicuous under clothing. The outer non-woven layer 20 provides increased comfort to the patient compared with imperforate polymeric films. Where the outer layer 20 is of a material that is only broken up by the action of an alkali, the bag can be worn safely while washing, swimming or undertaking similar activities where the outside of the bag may become wet. Where the outer layer 20 is of a kind that is broken down by water, the user would have to remove the bag if it were likely to become wet.

When the bag is full, it is removed from the body and closed by folding the adhesive flange 10 in half about its vertical diameter; excess air is expelled by squeezing through the vent 11. The bag 1 is then dropped into the wc pan so that the outer surface of the bag is contacted by the alkali and water mixture. It will be appreciated that a large proportion of the bag surface quickly becomes wetted by the surfactant and alkali, which starts to break up the non-woven layer 20 and the underlying layer 12. After a few minutes in the pan, the underlying layer 12 is dissolved or dispersed by the action of the alkali. Further details of the manner of disposal are given in GB 2257056.

The inner layer 18 is not affected by either water or alkali but it is so thin that, once it loses the structural support of the other layers 12 and 20, it has insufficient strength by itself to present an obstacle to flushing.

Flushing of the wc agitates the water in the pan helping further to break up the inner layer 18 or force it into more intimate contact with the bag contents. Any residual gas in the bag 1 escapes through the vent 11 or through ruptures in the bag as the wc is flushed, thereby allowing the contents of the bag and the remains of the bag itself to be flushed away without blockage.

The flange 10 is wc disposable and, in this respect may be of a material that becomes limp on contact with water and is of a suitable size that it is readily flushed away. For additional security, the flange could be water resistant but alkali disposable.

What I claim is:

1. A wc-disposable bag comprising two walls, said walls being made substantially from a material comprising: a first layer that is substantially entirely of alkali-soluble/water-resistant material; a second layer that is thinner than said first layer and is of water-resistant material bonded to one side of said first layer and presented inwardly of the bag; and a third layer bonded to said first layer on a side remote from said second layer, said third layer being presented outwardly of the bag and being of a non-woven material that is resistant to water but that breaks down when wetted by an alkaline liquid so that the bag is resistant to water but can be disposed of in a wc pan by adding an alkali to water in the wc pan, thereby causing said third layer to break down and allowing the alkali to break up or disperse said first layer, the thickness of said second layer being insufficient to impede flushing of the bag after break up or dispersion of said first and third layers but being sufficient to provide the major part of the odor barrier of the bag and to reduce odor transmission through the material to an acceptable level and the third layer providing mechanical reinforcement of the first layer to prevent stretching or deformation of the bag when exposed to water vapor.

2. The bag according to claim 1, wherein said first layer is of a carboxylated acrylic polymer.

3. The bag according to claim 1, wherein said second layer is of polyvinylidene chloride.

4. The bag according to claim 1, wherein said third layer when intact resists mechanical deformation of the bag by the weight of its contents.

5. The bag according to claim 1, wherein said third layer includes cellulose fibers.

6. The bag according to claim 1, wherein said third layer includes a binder of aqueous polyacrylate.

7. The bag according to claim 1, wherein the bag includes a coloring agent that colors water in the WC as the bag breaks down.

8. A wc-disposable bag comprising a front and rear wall, said walls being made substantially from a material comprising: a first layer that is substantially entirely of carboxylated acrylic polymer; a second layer that is thinner than said first layer and is of polyvinylidene chloride bonded to one side of said first layer and presented inwardly of the bag; and a third layer bonded to said first layer on a side remote from said second layer, said third layer being presented outwardly of the bag and being of a non-woven material that is resistant to water, the non-woven material including fibers in a binder of aqueous polyacrylate that is resistant to water but breaks down when wetted by an alkaline liquid so that the bag can be disposed of in a wc pan by adding an alkali to water in the wc pan, thereby causing said third layer to break down allowing the alkali to break up or disperse said first layer, and wherein the thickness of said second layer is insufficient to impede flushing of the bag after break up or dispersion of said first and third layers but is sufficient to provide the major part of the odor barrier of the bag and to reduce odor transmission through the material to an acceptable level and wherein the third layer providing mechanical reinforcement of the first layer to prevent stretching or deformation of the bag when exposed to water vapor.

* * * * *